United States Patent
Morris et al.

(10) Patent No.: US 7,270,650 B2
(45) Date of Patent: *Sep. 18, 2007

(54) CATHETER ANCHOR SYSTEM AND METHOD

(75) Inventors: Mary M. Morris, Moundsview, MN (US); Duane Gerald Frion, Brooklyn Center, MN (US); Jeff Novotny, Bethel, MN (US); Douglas Hankner, Fridley, MN (US); Stuart Lahtinen, Cambridge, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/017,336

(22) Filed: Dec. 20, 2004

(65) Prior Publication Data

US 2005/0101915 A1    May 12, 2005

Related U.S. Application Data

(63) Continuation of application No. 10/128,708, filed on Apr. 23, 2002, now abandoned.

(51) Int. Cl.
*A61M 5/32* (2006.01)
*A61B 17/56* (2006.01)
*A61B 17/58* (2006.01)
*A61F 2/30* (2006.01)

(52) U.S. Cl. .......... 604/177; 604/174; 606/72

(58) Field of Classification Search ........ 604/174–178, 604/180, 93.01, 284, 8, 9, 19, 890.1, 891.1, 604/164.04; 606/72, 73, 75; 128/898, DIG. 6, 128/DIG. 26, DIG. 5, 897
See application file for complete search history.

(56) References Cited

U.S. PATENT DOCUMENTS

| | | |
|---|---|---|
| 3,444,861 A | 5/1969 | Schulte |
| 4,250,880 A | 2/1981 | Gordon |
| 4,276,882 A | 7/1981 | Dickhudt et al. |
| 4,328,813 A | 5/1982 | Ray |
| 4,382,445 A | 5/1983 | Sommers |
| 4,435,174 A | 3/1984 | Redmond et al. |
| 4,645,492 A | 2/1987 | Weeks |
| 4,976,680 A | 12/1990 | Hayman et al. |
| 5,036,862 A | 8/1991 | Pohndorf |

(Continued)

FOREIGN PATENT DOCUMENTS

DE        10015323       11/2000

(Continued)

*Primary Examiner*—Matthew F. DeSanto
(74) *Attorney, Agent, or Firm*—Stephen W. Bauer; Mary P. Bauman; Michael J. Jaro

(57) ABSTRACT

A catheter system and method for intracranial infusion of therapeutic substances to a patient. An anchor formed of generally flexible, elastomeric material is used to mount the catheter to the outer surface of the skull of the patient. The anchor has a through hole for receiving the catheter, a channel, extending substantially from the through hole, into which a portion of the catheter may be inserted to retain the portion substantially parallel to the surface of the skull, and at least one flange for engaging the outer surface of the skull. An anchor clip may be provided to engage the anchor adjacent the through hole to further stabilize the catheter.

24 Claims, 4 Drawing Sheets

U.S. PATENT DOCUMENTS

| | | |
|---|---|---|
| 5,158,097 A | 10/1992 | Christlieb |
| 5,183,455 A | 2/1993 | Hayman et al. |
| 5,267,969 A | 12/1993 | Hirsch et al. |
| 5,344,439 A | 9/1994 | Otten |
| 5,364,367 A | 11/1994 | Banks et al. |
| 5,376,108 A | 12/1994 | Collins et al. |
| 5,464,446 A | 11/1995 | Dreessen et al. |
| 5,484,445 A * | 1/1996 | Knuth ........................ 606/129 |
| 5,584,874 A | 12/1996 | Rugland et al. |
| 5,722,959 A | 3/1998 | Bierman |
| 5,800,376 A | 9/1998 | Watson et al. |
| 5,810,781 A | 9/1998 | Bierman |
| 5,843,146 A | 12/1998 | Cross, Jr. |
| 5,843,150 A | 12/1998 | Dreessen et al. |
| 5,865,842 A | 2/1999 | Knuth et al. |
| 5,865,843 A | 2/1999 | Baudino |
| 5,916,200 A * | 6/1999 | Eppley et al. ............... 604/178 |
| 5,927,277 A | 7/1999 | Baudino et al. |
| 5,954,687 A | 9/1999 | Baudino |
| 5,961,519 A | 10/1999 | Bruce et al. |
| 6,044,304 A | 3/2000 | Baudino |
| 6,093,180 A * | 7/2000 | Elsberry ..................... 604/506 |
| 6,134,477 A | 10/2000 | Knuteson |
| 6,210,417 B1 | 4/2001 | Baudino et al. |
| 6,321,104 B1 | 11/2001 | Gielen et al. |
| 6,332,874 B1 | 12/2001 | Eliasen et al. |
| 6,482,182 B1 * | 11/2002 | Carroll et al. ............... 604/174 |
| 6,482,183 B1 * | 11/2002 | Pausch et al. ............... 604/174 |
| 6,491,664 B2 | 12/2002 | Bierman |
| 6,551,290 B1 | 4/2003 | Elsberry et al. |
| 6,554,802 B1 | 4/2003 | Pearson et al. |
| 6,719,727 B2 * | 4/2004 | Brimhall et al. ............. 604/177 |
| 6,786,892 B2 | 9/2004 | Bierman |
| 6,827,705 B2 | 12/2004 | Bierman |
| 7,090,661 B2 * | 8/2006 | Morris et al. ............... 604/177 |
| 2001/0011164 A1 | 8/2001 | Bierman |
| 2001/0039399 A1 | 11/2001 | Bierman |
| 2002/0049451 A1 * | 4/2002 | Parmer et al. .............. 606/108 |

FOREIGN PATENT DOCUMENTS

| | | |
|---|---|---|
| EP | 1016432 | 7/2000 |
| EP | 1048318 | 11/2000 |
| EP | 1048320 | 11/2000 |
| FR | 2806918 | 10/2001 |
| WO | WO90/03827 | 4/1990 |
| WO | WO96/33766 | 10/1996 |
| WO | WO97/15342 | 5/1997 |
| WO | WO98/08554 | 3/1998 |
| WO | WO98/48880 | 11/1998 |
| WO | WO99/55408 | 11/1999 |
| WO | WO 00/13743 | 3/2000 |
| WO | WO 02/13714 | 2/2002 |

* cited by examiner

Remove Stylet

Anchor

Anchor Clip

CATHETER ANCHOR SYSTEM AND METHOD

RELATED APPLICATIONS

This application is a continuation of U.S. patent application Ser. No. 10/128,708, filed Apr. 23, 2002 now abandoned, the entire contents of which is hereby incorporated herein by reference.

FIELD OF THE INVENTION

This application relates generally to implantable catheters, and more particularly to an anchor and method of use for mounting a catheter within a patient, for example, to the skull.

BACKGROUND OF THE INVENTION

Sometimes therapeutic substances, such as drugs, biologics, etc., are infused intraparenchymally or intracerebroventricularly to treat brain disorders, such as malignancies or neurodegenerative diseases. Co-assigned U.S. patent application Ser. No. 09/540,444, filed Mar. 31, 2000 (now U.S. Pat. No. 6,551,290), and Ser. No. 09/625,751, filed Jul. 26, 2000, (both incorporated herein by reference) disclose catheters that are particularly well suited for intraparenchymal or intraventricular convection-enhanced infusion of therapeutic substances. As used herein, "IPA" means intraparenchymal, "ICV" means intracerebroventricular, and "intraventricular" and "ventricles" refer to cerebroventricles.

Previously, intracranial catheters have been anchored to the periosteum, which is a fibrous membrane covering the surface of bone. The periosteum has not provided as much stability as desired, and movement of the catheter anchor may result in changes in the location of the catheter tip.

BRIEF SUMMARY OF THE INVENTION

Embodiments of this invention include a catheter system for intracranial delivery, such as intraparenchymal or ventricular delivery, of therapeutic substances to a patient. Embodiments of this system are adapted to anchor a flexible catheter in position relative to the skull for infusion of therapeutic substances, while allowing the anchor to be soft and pliable and thereby less likely to cause skin erosion. These embodiments are further adapted to be anchored to the skull bone rather than fragile periostium.

In a first embodiment, the catheter system generally comprises an elongate catheter (e.g., formed of silicone or polyurethane) having a lumen and at least one drug delivery orifice in fluid communication with the lumen, and an anchor formed of generally flexible, elastomeric material for mounting the catheter to the outer surface of the skull of the patient. The anchor has a through hole for receiving the catheter, and a channel extending substantially from the through hole. A portion of the catheter may be inserted into the channel to retain the portion substantially parallel to the surface of the skull. At least one flange is provided for engaging the outer surface of the skull. At least one substantially rigid standoff is mounted in the flange, with the standoff having an opening for receiving a fastener to fasten the anchor to the skull.

Most preferably, the anchor is adapted to flex and comply with adjacent tissue. For example, the generally flexible, elastomeric material of the anchor may comprise silicone.

Preferably, two flanges are provided on the anchor, with at least one standoff mounted in each flange. For example, the standoffs may be insert molded in the flanges of the anchor. The standoffs may be formed of titanium or titanium alloy. The standoffs are preferably substantially annular and have an undercut or circumferential channel helping to retain the standoff in the flange.

Also, preferably, the anchor has a body in which the through hole and channel are formed, with the body being generally elongate and coaxial with the channel. The body extends in a direction generally perpendicular to the through hole and openings of the standoffs, and the flanges extending substantially in opposite directions substantially perpendicular to the body. The channel is substantially perpendicular to the through hole.

In certain embodiments of the invention, an anchor clip is also provided, which is adapted to be fastened to the outer surface of the skull to stabilize the catheter relative to the skull. The anchor clip engages the body of the anchor adjacent the through hole. For example, the anchor clip may be generally V-shaped having two legs each having a free end and a joined end joined with the other leg. The free end of each leg has an opening for receiving a fastener to mount the anchor clip to the skull. The anchor clip also having a slot adjacent the joined ends of the legs for engagement with the anchor to stabilize the anchor.

The catheter system is preferably used in combination with an implantable therapeutic substance infusion device, such as an implantable drug pump. The catheter may be directly or indirectly connected with the implantable therapeutic substance infusion device for infusion of therapeutic substance from the implantable therapeutic substance infusion device through the lumen and orifice(s) of the catheter. Indirect connection includes without limitation intermediate connectors or tubing sections.

In another aspect of the invention, a method of implanting the catheter system comprises: (a) inserting the catheter into the parenchyma or a ventricle; (b) mounting the anchor on the catheter and the skull of a patient to retain the catheter in position; and (c) infusing a therapeutic agent into the parenchyma or a ventricle for treatment of brain tissue.

Preferably, the anchor is mounted on the catheter and the skull of a patient to retain the catheter in position by: (a) inserting the catheter into the through hole of the anchor; (b) sliding the anchor along the catheter into engagement with the skull; (c) inserting a fastener through each opening of the standoff to fasten the anchor to the skull; and (d) placing the anchor in the channel. The catheter may also be sutured in the channel.

DETAILED DESCRIPTION OF THE INVENTION

Figure 1:
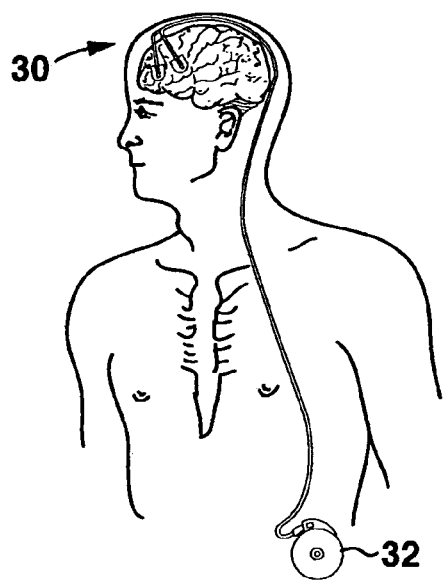
FIG. 1 illustrates the use of an embodiment of the catheter system in combination with an implantable therapeutic substance infusion device (e.g., drug pump).

A catheter system 30 of the invention is shown in FIG. 1 in combination with an implantable therapeutic substance infusion device, such as an implantable drug pump 32 ("IDP"). FIG. 1 illustrates use of the catheter system to infuse therapeutic substances stored in the reservoir of the IDP 32 into the parenchyma but the system could also be used to infuse such substances into other regions, such as cerebroventricles.

Figure 2:
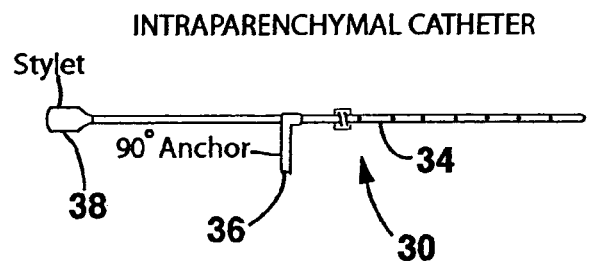
FIG. 2 is a side view of an embodiment of the catheter system.

FIG. 2 illustrates further details of the catheter system 30, which comprises the catheter 34, anchor 36 and stylet 38. The stylet 38 provides sufficient rigidity to facilitate handling the catheter 34, which is preferably very soft and flexible. The stylet 38 is removed after the catheter 34 has been moved into position. Various markings may be provided along the catheter 34 is facilitate positioning and implantation.

Figure 3:
FIG. 3 is a side view of a catheter with portions cut away to illustrate details.

A preferred catheter 34 for use in the catheter system is the catheter disclosed in U.S. patent application Ser. No. 09/625,751, filed Jul. 26, 2000, which is incorporated herein by reference. FIG. 3 illustrates details of a preferred embodiment of the catheter in which a multiplicity of very small diameter orifices or openings are provided through the wall of the catheter. The preferred orifice arrangement relative to the diameter of the catheter lumen ensures that fluid is delivered fairly evenly across the orifices. The catheter 34 may be formed, for example, of silicone or polyurethane.

Figure 4:
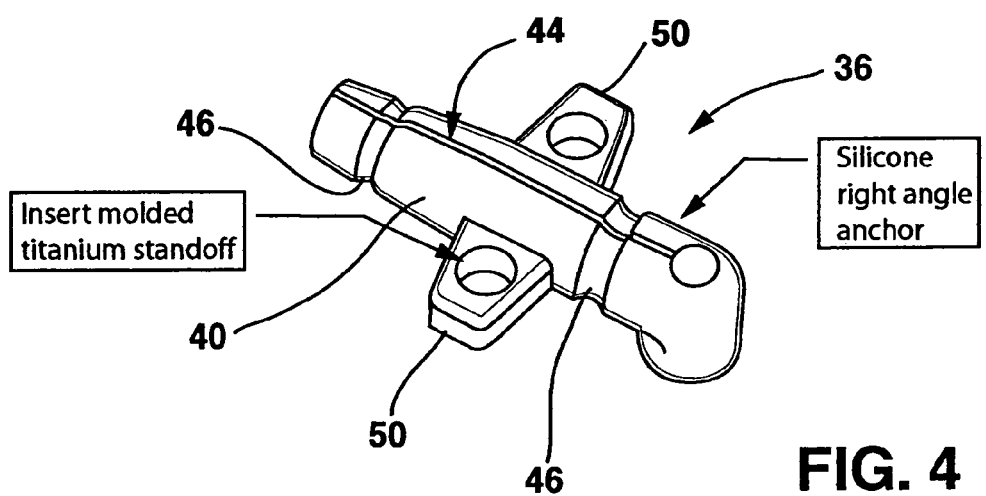
FIG. 4 is a perspective view of an embodiment of an anchor of the system.
Figure 5:
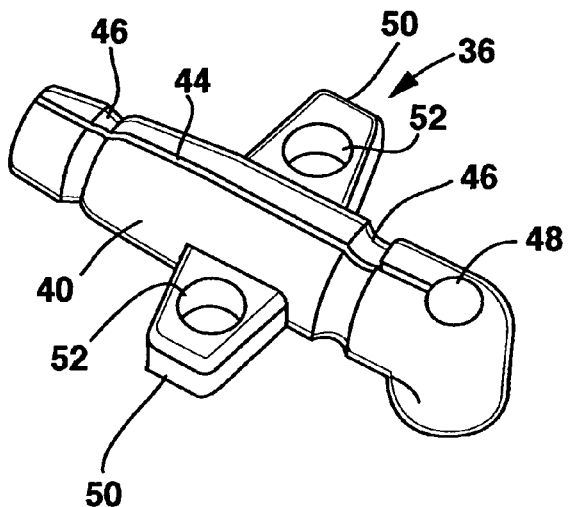
FIG. 5 is another perspective view of an anchor.
Figure 7:
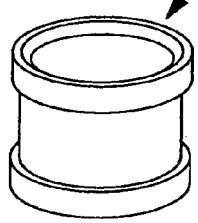
FIGS. 7 and 8 are perspective and cross sectional views of a standoff of FIG. 6.
Figure 8:
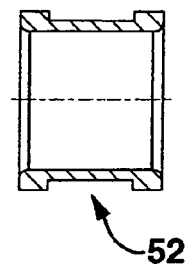
Figure 6:
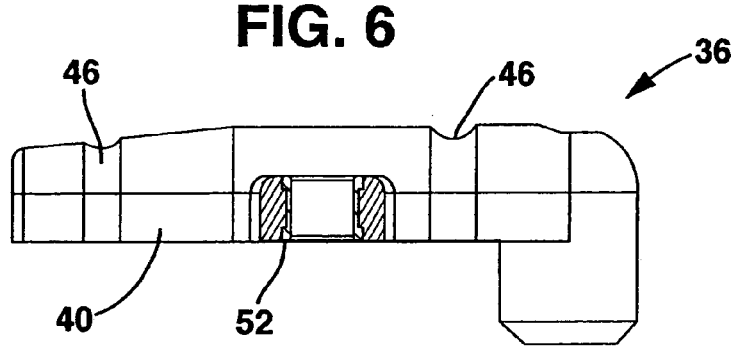
FIG. 6 is a side elevation of the anchor of FIGS. 4-5 with a portion cut away to illustrate details of an embodiment of a rigid standoff.
Figure 9:
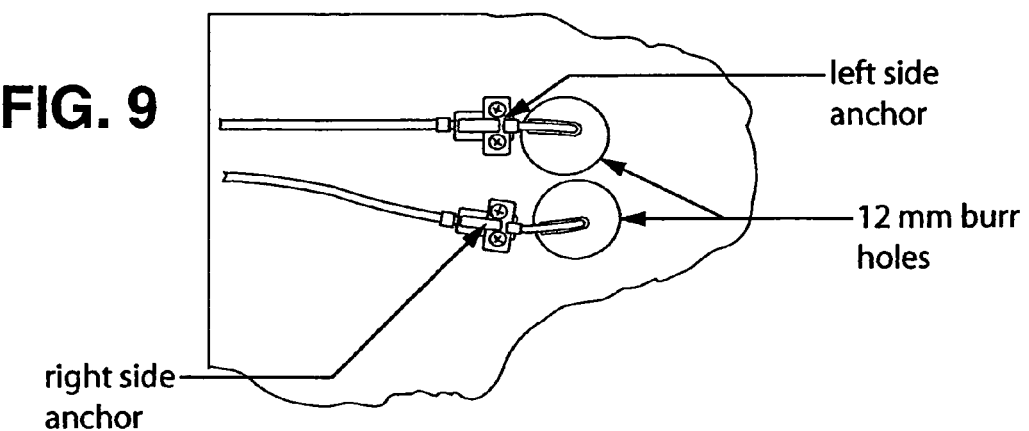
FIG. 9 is a photograph of an embodiment of the catheter system being implanted.

As illustrated in FIGS. 4-6, a preferred embodiment of the anchor 36 comprises a soft, pliable elongate body 40 having a generally circular cross section. A longitudinal channel 42 is provided in the body 40 with a slot 44 open along the top of the channel 42 to allow a catheter 34 to be inserted through the slot 44 into the channel 42. The catheter-receiving channel 42 is sized, configured and adapted to receive the catheter 34 to hold the catheter 34 generally parallel or tangent to the surface of the skull. Two annular channels 46 may be provided on the body 40 for receiving sutures (not shown) to further lock the catheter 34 in the channel. The anchor 34 is preferably formed of an elastomeric material, such as silicone or polyurethane.

A through hole 48 is provided adjacent the proximal end of the body 40 of the anchor 34. The catheter 32 may be inserted into, and the anchor 34 slide along the catheter 32, to position the anchor 34 against the skull. Alternatively, the anchor 34 may be positioned adjacent the burr hole and the catheter 32 slide through the through hole 48 of the anchor 34 into position. In yet another alternative, the anchor 34 may be designed, for example, by the addition of a slit (not shown) to allow the anchor 34 to be attached to the catheter 32 in the lateral or radial direction rather than, or in addition to, being slide longitudinally relative to the catheter 32.

The through hole 48 and channel 42 are substantially oriented at right angles to one another. The longitudinal channel 42 and through hole 48 are connected so that the catheter 32 can be bent at about a right angle to be held in the channel 42 in an orientation generally parallel or tangent to the surface of the skull.

At least one flange or tab, but preferably two flanges 50 extend in generally opposite directions from the body 40. The flanges 50 are integrally molded as one continuous piece with the body 40. The flanges 50 are set back from the proximal end of the body 40 (i.e. the end with the through hole 48) so that the flanges 50 may rest on bone adjacent a burr hole (see, e.g., FIG. 13) with the through hole 48 held over the burr hole. The anchor 34 maintains the through hole 48 substantially at a predetermined orientation and location relative to the skull and burr hole. For example, the through hole 48 is maintained substantially at a perpendicular orientation relative to the plane of the burr hole.

At least one generally rigid standoff 52 is provided on each flange 50 as illustrated in FIGS. 4-8. The standoffs 52 are adapted to receive a fastener, such as a surgical screw, to fasten the anchor 34 to bone. The standoffs 52 are formed of material that is much more rigid than the soft, pliable silicone preferred for the anchor 34. Examples of suitable materials include titanium and titanium allow, although other materials could alternatively be employed. Each standoff 52 is generally cylindrical with an undercut or annular channel provided along the circumferential surface to help lock the standoff 52 on the flange 50, for example, by insert molding the standoff 52. Alternatively, the standoffs 52 can be fixed in the flanges 50 by other suitable techniques, including without limitation bonding. Each standoff 52 includes a central bore or opening for receiving a fastener, such as a screw.

The through hole 48 constitutes one preferred embodiment of an orienting means for slidably receiving the catheter and orienting the catheter relative to the parenchyma. The longitudinally-extending, catheter-receiving channel 42 constitutes one preferred embodiment of a means, generally adjacent the orienting means, for laterally receiving the catheter to retain a portion of the catheter substantially parallel to the surface of the skull.

The flanges 50 constitute a preferred embodiment of a generally flexible skull-engaging means for engaging the outer surface of the skull. The standoffs 52 constitute a preferred embodiment of a substantially rigid means in the skull engaging means for receiving a fastener to fasten the anchor to the skull.

An optional anchor clip 54 (see, e.g., FIGS. 14-17) may also be provided, which is adapted to be fastened to the outer surface of the skull to stabilize the catheter 32 relative to the skull. The anchor clip 54 engages the body 40 of the anchor 34 adjacent the through hole 48. The body of the anchor 40 preferably includes a downwardly extending annular portion coaxial with the through hole which may be received in a retaining slot 56 in the anchor clip 54. Suitable materials for the anchor clip include, for example, polysulfone.

Most preferably, the anchor clip 54 is generally V-shaped, with two legs 58 each having a free end and a joined end forming an apex of the clip 54 with the other leg. The free end of each leg has an opening 60 for receiving a fastener to mount the anchor clip 54 to the skull. The retaining slot 56 is formed at the apex of the clip 54 adjacent the joined ends of the legs. The retaining slot 56 engages the anchor 34 to stabilize the anchor 34.

Figure 10:
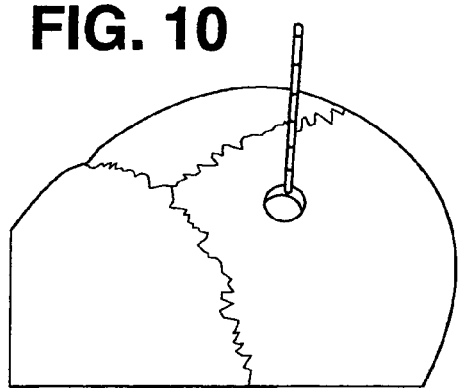
FIGS. 10-21 are illustrations showing an embodiment the catheter system and a method of implanting the catheter system.
Figure 11:
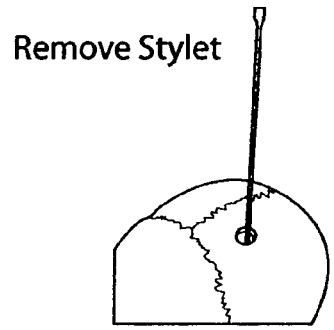

FIGS. 10-21 illustrate various aspects of a preferred method of implanting a catheter anchor system. As illustrated in FIG. 10, this method includes (a) forming (cutting, drilling, etc.) a burr hole through the skull of a patient, and (b) inserting a catheter into the parenchyma or ventricle of the patient. The catheter 32 is preferably soft and conformable, and rigidity is provided temporarily by a rigid stylet to facilitate controlled insertion. In addition, imaging and various guidance means, such as stereotactic or non-stereotactic frames may be employed. After the catheter 32 is in position, the stylet is removed as illustrated in FIG. 11.

Figure 12:
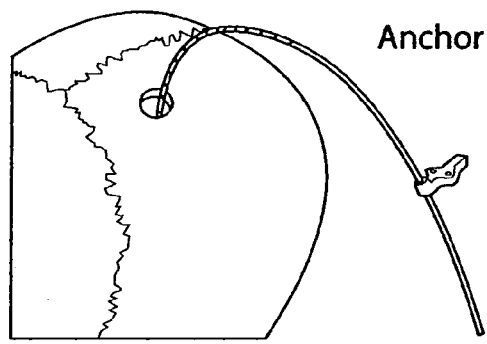
Figure 13:
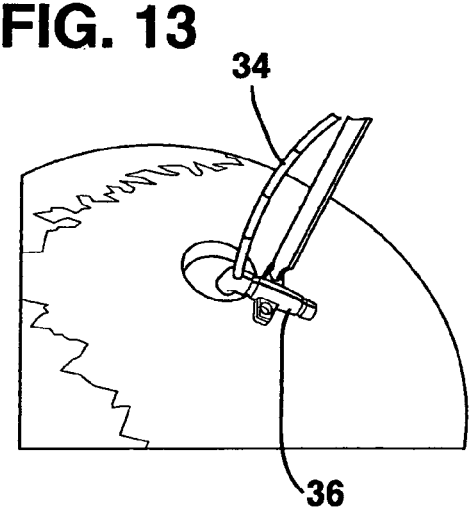

A catheter anchor 34 is then placed on the catheter 32 and slide down the catheter 32 into position against the skull as illustrated in FIGS. 12 and 13. Alternatively, the anchor 34 may be positioned adjacent the burr hole and the catheter 32 slide through the through hole 48 of the anchor 34 into position. FIG. 13 illustrates screwing surgical screws through the standoffs 52 to fasten the anchor 34 to the skull.

Figure 14:
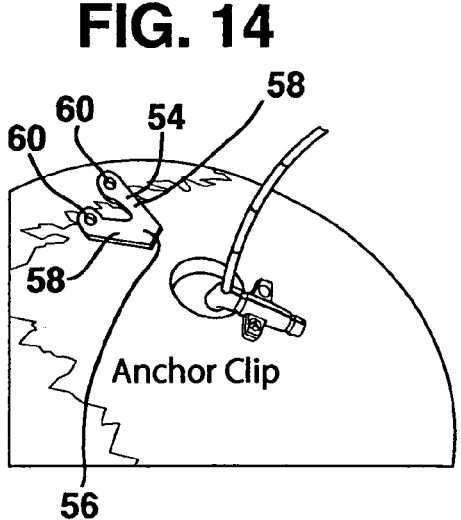
Figure 15:
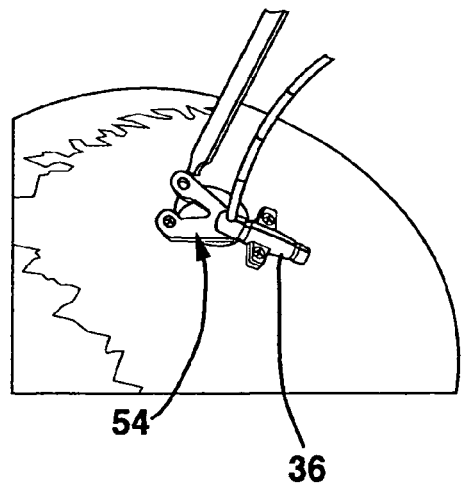

An optional anchor clip 54 is attached to the anchor 34 and skull as illustrated in FIGS. 14 and 15 to help stabilize the proximal end of the anchor 34 to help stabilize the catheter 32 relative to the skull.

Figure 16:
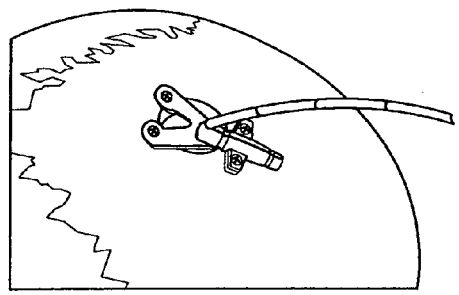
Figure 17:
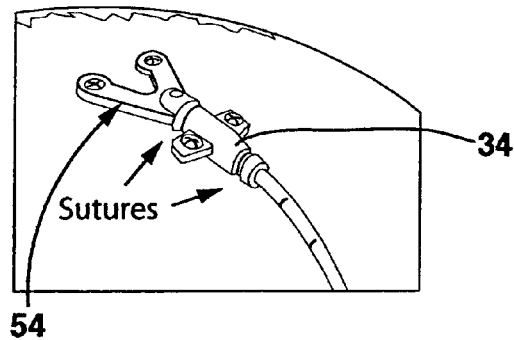
Figure 18:
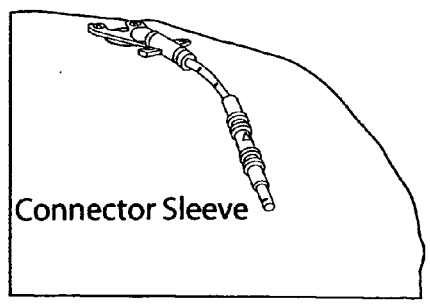
Figure 19:
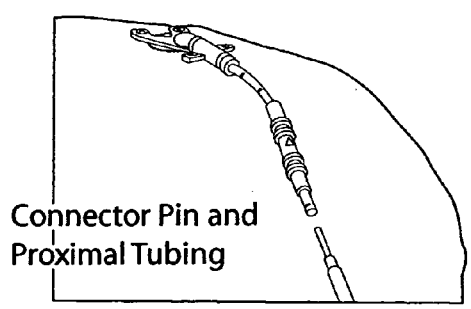
Figure 20:
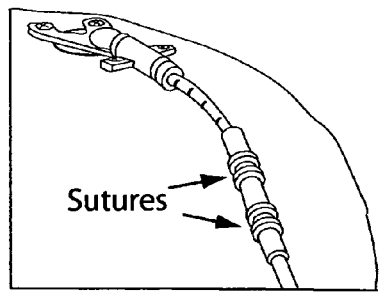
Figure 21:
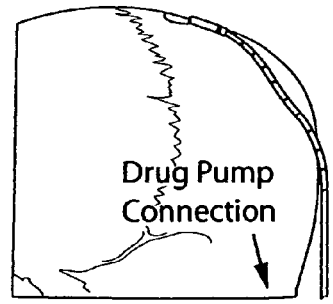

The catheter 32 is then laid down through the top slot of the anchor 34 into the catheter-receiving channel 42, and sutures may be employed to retain the catheter 32 in the channel 42 as illustrated in FIGS. 16 and 17.

FIGS. 18-21 illustrate use of a connector sleeve, connector pin, proximal tubing and sutures to connect the catheter 32 to a implantable drug pump or other implantable therapeutic substance infusion device.

Thus, embodiments of the catheter anchor system and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable anchor system for an elongate implantable catheter used in intracranial delivery of therapeutic substances to a patient, the anchor system comprising:
    an anchor for mounting the catheter to the outer surface of the skull of the patient, the anchor including:
       a body formed of generally flexible, elastomeric material that is adapted to flex and comply with adjacent tissue, the body having:
       a through hole for receiving the catheter and orienting the catheter relative to the parenchyma,
       a channel, extending substantially from the through hole in a direction generally perpendicular to the through hole, into which a portion of the catheter may be inserted to retain the portion substantially parallel to the surface of the skull, wherein the channel is open along a slot formed in a top portion thereof through which the portion of the catheter may be inserted into the channel; and
       at least one flange for engaging the outer surface of the skull, the flange including opposite major surfaces; and
       at least one substantially rigid standoff mounted in the flange, the standoff including an opening and the standoff being exposed through the opposite major surfaces of the flange; and
       a bone screw extending through the opening of the standoff for fastening the anchor to a surface of the skull.

2. The anchor system of claim 1 wherein the standoff is substantially annular and has an undercut or circumferential channel helping to retain the standoff in the flange.

3. The anchor system of claim 2 in which:
    the at least one flange comprises two flanges extending in opposite directions from the channel;
    the at least one substantially rigid standoff comprising at least one standoff mounted in each flange; and
    the channel is substantially perpendicular to the through hole.

4. The anchor system of claim 3 in which the standoffs are insert molded in the flanges of the anchor.

5. The anchor system of claim 4 in which the generally flexible, elastomeric material comprises silicone, and the standoffs are formed of titanium or titanium alloy.

6. The anchor system of claim 3 in which the body is generally elongate and coaxial with the channel, the body extending in a direction generally perpendicular to the through hole and openings of the standoffs, the flanges extending substantially in opposite directions substantially perpendicular to the body.

7. A catheter system for intracranial delivery of therapeutic substances to a patient, the system comprising:
    an elongate catheter having a lumen and at least one drug delivery orifice in fluid communication with the lumen;
    the anchor system of claim 1.

8. The catheter system of claim 7 wherein the catheter is received in the through hole such that the system is adapted to orient the catheter relative to the parenchyma, and a portion of the catheter retained within the channel such that the catheter system is adapted to maintain the portion of the catheter substantially parallel to the surface of the skull a channel.

9. The catheter system of claim 7 in which the catheter is formed of silicone or polyurethane.

10. A system for intracranial delivery of therapeutic substances to a patient, the system comprising:
    the catheter system of claim 9; and
    an implantable therapeutic substance infusion device, the catheter being directly or indirectly connected with the implantable therapeutic substance infusion device for infusion of therapeutic substance from the implantable therapeutic substance infusion device through the lumen and orifice(s) of the catheter.

11. A catheter system for intracranial delivery of therapeutic substances to a patient, the system comprising:
    an elongate catheter having a lumen and at least one drug delivery orifice in fluid communication with the lumen;
    an implantable anchor system comprising:
       an anchor for mounting the catheter to the outer surface of the skull of the patient, the anchor including:
          a body formed of generally flexible, elastomeric material, the body having:
             a through hole for receiving the catheter and orienting the catheter relative to the parenchyma,
             a channel, extending substantially from the through hole in a direction generally perpendicular to the through hole, into which a portion of the catheter may be inserted to retain the portion substantially parallel to the surface of the skull; and
             at least one flange for engaging the outer surface of the skull, the flange including opposite major surfaces; and
          at least one substantially rigid standoff mounted in the flange, the standoff including an opening and the standoff being exposed through the opposite major surfaces of the flange, wherein the standoff is substantially annular and having an opening for receiving a fastener to fasten the anchor to the skull, and an undercut or circumferential channel helping to retain the standoff in the flange; and
          a bone screw extending through the opening of the standoff for fastening the anchor to a surface of the skull.

12. The catheter system of claim 11 in which:
the at least one flange comprises two flanges extending in opposite directions from the channel;
the at least one substantially rigid standoff comprising at least one standoff mounted in each flange; and
the channel is substantially perpendicular to the through hole.

13. The catheter system of claim 12 wherein the flange includes opposite major surfaces, and the standoff is exposed through the opposite major surfaces.

14. The catheter system of claim 13 in which the anchor is adapted to flex and comply with adjacent tissue, and the standoffs are insert molded in the flanges of the anchor.

15. The catheter system of claim 14 in which the generally flexible, elastomeric material comprises silicone or polyurethane, and the standoffs are formed of titanium or titanium alloy.

16. The catheter system of claim 13 in which the body is generally elongate and coaxial with the channel, the body extending in a direction generally perpendicular to the through hole and openings of the standoffs, the flanges extending substantially in opposite directions substantially perpendicular to the body.

17. A system for intracranial delivery of therapeutic substances to a patient, the system comprising:
the catheter system of claim 11; and
an implantable therapeutic substance infusion device, the catheter being directly or indirectly connected with the implantable therapeutic substance infusion device for infusion of therapeutic substance from the implantable therapeutic substance infusion device through the lumen and orifice(s) of the catheter.

18. An implantable anchor system for an elongate implantable catheter used in intracranial delivery of therapeutic substances to a patient, the anchor system comprising:
an anchor for mounting the catheter to the outer surface of the skull of the patient, the anchor including:
a body formed of generally flexible, elastomeric material that is adapted to flex and comply with adjacent tissue, the body having:
a through hole for receiving the catheter and orienting the catheter relative to the parenchyma,
a channel, extending substantially from the through hole in a direction generally perpendicular to the through hole, into which a portion of the catheter may be inserted to retain the portion substantially parallel to the surface of the skull, wherein the channel is open along a slot formed in a top portion thereof through which the portion of the catheter may be inserted into the channel;
at least one flange for engaging the outer surface of the skull, the flange including opposite major surfaces; and
a bone screw extending through the flange for fastening the anchor to a surface of the skull.

19. The anchor system of claim 18 wherein the anchor further comprises at least one substantially rigid standoff mounted in the flange, the standoff including an opening and the standoff being exposed through the opposite major surfaces of the flange.

20. The anchor system of claim 19 wherein the standoff is substantially annular and has an undercut or circumferential channel helping to retain the standoff in the flange.

21. The anchor system of claim 20 in which:
the at least one flange comprises two flanges extending in opposite directions from the channel;
the at least one substantially rigid standoff comprising at least one standoff mounted in each flange; and
the channel is substantially perpendicular to the through hole.

22. The anchor system of claim 21 in which the standoffs are insert molded in the flanges of the anchor.

23. The anchor system of claim 21 in which the generally flexible, elastomeric material comprises silicone, and the standoffs are formed of titanium or titanium alloy.

24. The anchor system of claim 21 in which the body is generally elongate and coaxial with the channel, the body extending in a direction generally perpendicular to the through hole and openings of the standoffs, the flanges extending substantially in opposite directions substantially perpendicular to the body.

* * * * *